March 2, 1971 F. K. ISHIDA Plant Pat. 3,031

AZALEA PLANT

Filed April 21, 1969

INVENTOR.

FRANK K. ISHIDA,

By Edmond F. Shanahan

ATTORNEY.

United States Patent Office

Plant Pat. 3,031
Patented Mar. 2, 1971

3,031
AZALEA PLANT

Frank K. Ishida, South Gate, Calif., assignor to Monrovia Nursery Company, Azusa, Calif.

Filed Apr. 21, 1969, Ser. No. 818,159
Int. Cl. A01h *5/00*
U.S. Cl. Plt.—57 1 Claim The present discovery relates to a new and distinct variety of the Rhododendron genus, Azalea species characterized as to novelty by its vigorous growth, its abundant dark green foilage and its brilliantly colored flowers that stand out well against the dark green foliage.

Figures 1, 2:
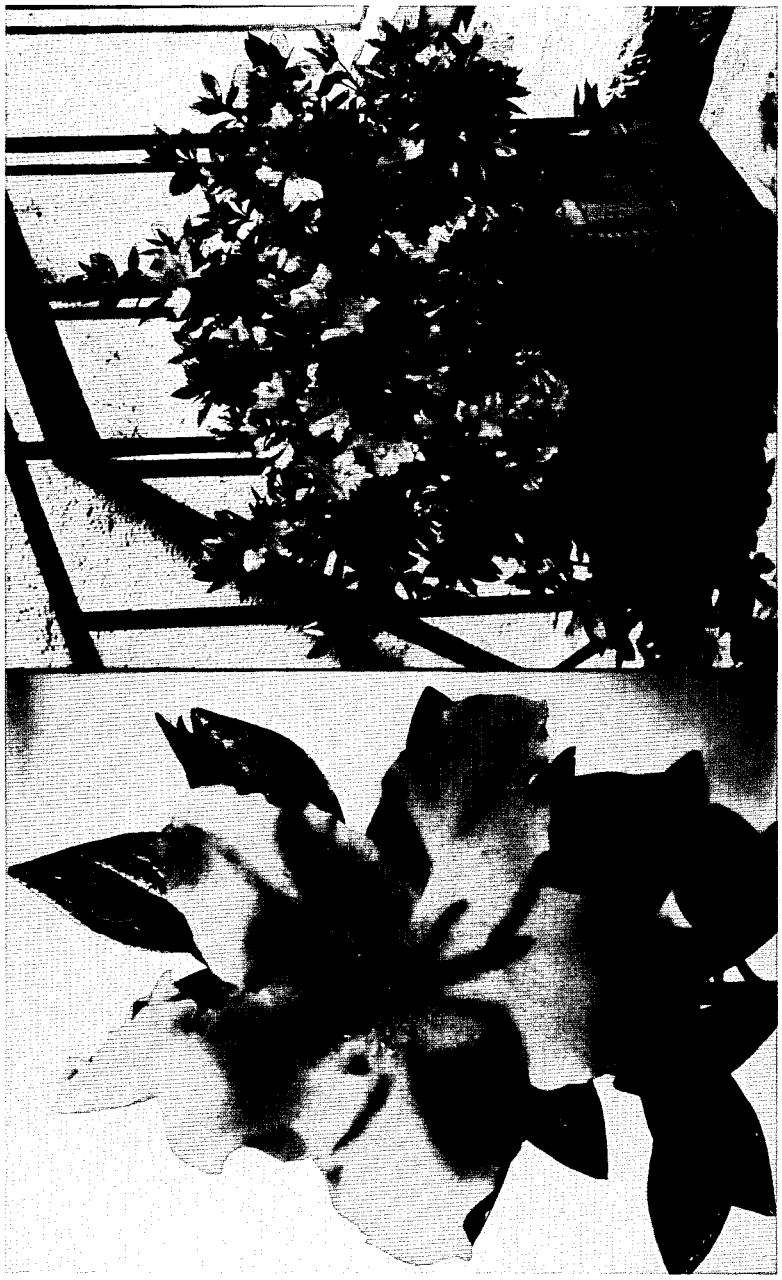

The new variety was discovered by me growing as a chance seedling in a bed of azalea seedlings being grown by me at my nursery in southern California from some seed collected by my father in Japan. Neither the pollen parent or the seed parent of this plant is known. The plant was selected by me when it first flowered late in 1954, because of its large brilliantly colored red flowers and dark green foliage. The plant has been asexually propagated by me and all of its descendants have shown the same characteristics which show that the descendants are true and that the new variety has become well established. It does not reproduce true from seed.

A flower and plant of the new variety are shown in full color in the accompanying illustration.

A detailed description of the new variety follows, and to facilitate identification of the important colors, the color terminology adopted by the British Horticultural Color Charts has been followed.

THE PLANT

Parentage: Chance seedling resulting from open pollination.

Seed parent.—Unknown.

Pollen parent.—Unknown.

Growth: The plant is of vigorous upright habit of growth with a dense branching habit. Branches are spreading and ascending and are well clothed with foliage. The ultimate height of the plant is not known, but from observations of maturing plants it is expected to reach 7 to 8 feet in height and from 5 to 6 feet in spread.

Branches: New growth is of a light green in color gradually changing to a reddish-brown and at full maturity a grayish-brown. The new growth is densely hairy which disappears as the branch matures.

Growth habit: Branching starts from just above the ground level and has a tendency to be spreading and ascending.

Foliage: The leaves are of good substance and are a semi-glossy dark green in color.

Shape: The leaves are best described as being elliptic in shape. Margins are entire and ciliate. Apex is mucronulate base is attenuate.

Size: Leaves are from 1½ to 2⅛ inches in length and from ⅝ to 1 inch in width. Petiole is from 3/16 to ¼ inch in length.

Arrangement: Leaves are alternate on the branches.

Veins: Midrib on the upperside is recessed and strigose hairy only slightly lighter in color than the blade. Midrib underneath is prominent and strigose hairy.

Color: New leaves are a semi-glossy 0960 Spinach Green above, and slightly darker than 860 Scheeles Green beneath. Mature leaves are a semi-glossy and slightly darker than 0960 Spinach Green above and 0960/3 beneath. On both surfaces new and mature leaves are remotely strigose hairy.

THE FLOWER

The plant will set an occasional flower from early September until late February reaching its peak of bloom in April, tapering off into May.

Form: Flowers are single with a natural spread of 3½ to 3¾ inches, with a depth of 2 inches.

Petals: Petals are five in number, standard petal 1½ inches upper and lower wing petals 1⅝ inches, tube 1 inch.

Stamens: In all flowers observed 10 stamens were found, usually 8 were up to 1¾ inches in length while 2 were 1⅛ inches in length. Filaments 722 Cherry in color, anthers purple.

Pistil: Pistil is 1½ inches in length, red in color.

Color: The flower is of one color 025 Spiraea Red. The standard petal and the two upper wing petals are blotched with dark purple.

I claim:

1. A new and distinct variety of azalea plant, substantially as described and illustrated herein, and characterized particularly by the large size and unique coloring of its flowers, vigorous growth, and dense, dark green foliage.

No references cited.

ROBERT E. BAGWILL, Primary Examiner